US 6,607,515 B2

(12) United States Patent
Glaug et al.

(10) Patent No.: US 6,607,515 B2
(45) Date of Patent: Aug. 19, 2003

(54) ABSORBENT ARTICLE WITH SINGLE ATTACHMENT MEANS ON EACH SIDE OF ARTICLE

(75) Inventors: Frank S. Glaug, Chester Springs, PA (US); Robert T. Cole, Jackson, NJ (US); Pamela S. Peters, Harleysville, PA (US)

(73) Assignee: Tyco Healthcare Retail Services AG (CH)

( * ) Notice: Subject to any disclaimer, the term of this patent is extended or adjusted under 35 U.S.C. 154(b) by 47 days.

(21) Appl. No.: 10/005,687

(22) Filed: Nov. 8, 2001

(65) Prior Publication Data

US 2003/0088225 A1 May 8, 2003

(51) Int. Cl.[7] ................................. A61F 13/15
(52) U.S. Cl. ........................ 604/385.01; 604/385.25
(58) Field of Search ................. 604/385.01, 385.25, 604/396, 386, 387, 389, 392, 394, 385.27

(56) References Cited

U.S. PATENT DOCUMENTS

| | | |
|---|---|---|
| 4,738,675 A | 4/1988 | Buckley et al. |
| 4,764,234 A | 8/1988 | Smits et al. |
| 4,764,242 A | 8/1988 | Gressick et al. |
| 4,795,451 A | 1/1989 | Buckley |
| 4,804,379 A | 2/1989 | Toth et al. |
| 4,900,318 A | 2/1990 | Toth |
| 4,906,243 A * | 3/1990 | Dravland ................ 604/394 |
| 5,071,415 A | 12/1991 | Takemoto |
| 5,263,948 A | 11/1993 | Karami et al. |
| 5,263,949 A | 11/1993 | Karami et al. |
| 5,308,344 A | 5/1994 | Toth |
| 5,399,219 A * | 3/1995 | Roessler et al. ............ 156/259 |
| 5,520,673 A | 5/1996 | Yarbrough et al. |
| 5,649,919 A | 7/1997 | Roessler et al. |
| 5,817,086 A | 10/1998 | Kling |
| 5,876,390 A | 3/1999 | Hall et al. |
| 5,947,948 A | 9/1999 | Roe et al. |
| 6,010,586 A * | 1/2000 | Suprise ................ 156/73.1 |
| 6,049,024 A * | 4/2000 | Thomas et al. ............ 604/367 |

* cited by examiner

Primary Examiner—Weilun Lo
Assistant Examiner—Jacqueline Stephens
(74) Attorney, Agent, or Firm—Caesar, Rivise, Bernstein, Cohen & Pokotilow, Ltd.

(57) ABSTRACT

A disposable absorbent brief. The brief includes a back section having a pair of ears, each having a single fastening tape mounted thereon, and a front section having a pair of ears for releasable securement by the fastening tapes of the front section. The portions of the brief located between the ears are in the form of an opposed pair of central edges. The central edges are ergonomically contoured so that when the brief's ears are secured to each other the central edges and contiguous ears form respective high-cut leg openings for the wearer, with portions of the brief providing enhanced coverage of the wearer's buttocks.

24 Claims, 4 Drawing Sheets

ABSORBENT ARTICLE WITH SINGLE ATTACHMENT MEANS ON EACH SIDE OF ARTICLE

FIELD OF THE INVENTION

This invention relates generally to disposable absorbent articles for adult persons, and more specifically to disposable protective underwear, e.g., briefs, which offer various advantages over the prior art, e.g., are more convenient to use, provide improved body conformance, comfort, reduced leakage, simplicity of construction and reduced cost.

BACKGROUND OF THE INVENTION

As populations continue to increase in longevity, incontinence, a problem of age presents a need for fluid control in undergarments. In particular, adult incontinence represents a transition from underwear to the use of some type of absorbent article to be added to the underwear or to completely replace it. For moderate-to-heavy incontinence needs a variety of disposable diaper designs are commercially available. Nevertheless certain deficiencies have been recognized in diapers that are currently found in the market place. For example, many of them, particularly high capacity designs, are thick and bulky, thus rendering concealment difficult. Moreover many of such prior art absorbent articles are complex in construction and are somewhat difficult to put on.

The patent literature includes various diapers and other absorbent disposable articles which are arranged to be worn to absorb and retain waste products from a person (child or adult). See for example, U.S. Pat. No. 4,738,675 (Buckley et al.); U.S. Pat. No. 4,900,318 (Toth); U.S. Pat. No. 5,071,415 (Takemoto); U.S. Pat. No. 5,308,344 (Toth); U.S. Pat. No. 5,263,949 (Karami et al.); U.S. Pat. No. 5,520,673 (Yarbrough et al.); U.S. Pat. No. 5,649,919 (Roessler et al.); U.S. Pat. No. 5,876,390 (Hall et al.); U.S. Pat. No. 5,817,086 (Kling); and U.S. Pat. No. 5,947,848 (Roe et al.), all of which disclose absorbent articles which may be of various shapes, such as rectangular, trapezoidal, T-shaped, I-shaped, hour-glass shaped, but which include various elastic components and/or other structural features, such as adhesive mounting tabs.

In addition to the absorbent articles described in the aforementioned prior art patents, various absorbent articles of this type are commercially available from several manufacturers. One such commercially available absorbent disposable undergarment or brief is that sold by a division of the assignee of the subject invention, namely, Tyco Healthcare Retail Group, Inc. (previously known as Kendall Confab Retail Group) under the trademark "Supreme" adult briefs. An illustration of a typical prior art Supreme adult brief 10 mounted in position on a person is shown in the side view of FIG. 1. As can be seen in that figure the side portions 11 and 12 of the brief are of generally rectangular shape and are secured together by a pair of fastening tapes 13 and 14 on each side of the brief. The rectangular shape of the overlapping side portions may result in the imposition of tension and stresses in the fastened areas contiguous with the legs of the wearer, particularly when the wearer is sitting down. This action, may have the effect of detracting somewhat from the comfort of the undergarment. Moreover, in the area of the sides of the wearer's buttocks merging with the wearer's legs the back portions of the undergarment are of a less than ideal ergonomic shape, e.g., they are a relatively right-angled corner, which may detract from wearer comfort.

Thus, while the prior art disposable protective undergarments may be generally suitable for their intended purposes, they nevertheless leave something to be desired from the standpoints of ease of use or mounting, good conformance to the body of the wearer, resistance to leakage, comfort, simplicity of construction and reduced manufacturing cost.

SUMMARY OF THE INVENTION

A protective underwear, e.g., brief, arranged to be worn by a person to trap and collect loose or liquid waste products of the person. The underwear has a front section, a back section and a central section. The front section has a front top edge and a pair of front side edges. The back section has a back top edge and a pair of back side edges. The central section has a pair of central side edges and is located between the front and back sections.

The back section includes a pair of fastening members, e.g., releasably securable tapes, secured thereto, with one of the fastening members extending beyond one of the back side edges and the other of the fastening members extending beyond the other of the back side edges.

Each of the central side edges has a first central edge region and a second central edge region. The first central edge region of each central side edge is of a concave arcuate shape, while the second central edge region is of a generally S-shape having a concave portion and a convex portion. The first central edge regions are contiguous with respective ones of the front side edges, with the convex portions of the second central edge regions being contiguous with respective ones of the first central edge regions and with the concave portions of the second central edge regions being contiguous with respective ones of the back side edges.

The two fastening members are arranged to be secured to respective portions of the front section of the underwear to mount the underwear in place on the wearer, with the central section being located adjacent the wearer's crotch. When so mounted each of the first central regions of the central side edges provides a high cut area contiguous with the front of the wearer's leg adjacent the wearer's crotch and each of the convex portions of the second central edge regions provides substantial coverage of the wearer's buttocks.

DETAILED DESCRIPTION OF THE PREFERRED EMBODIMENT

Figure 2:
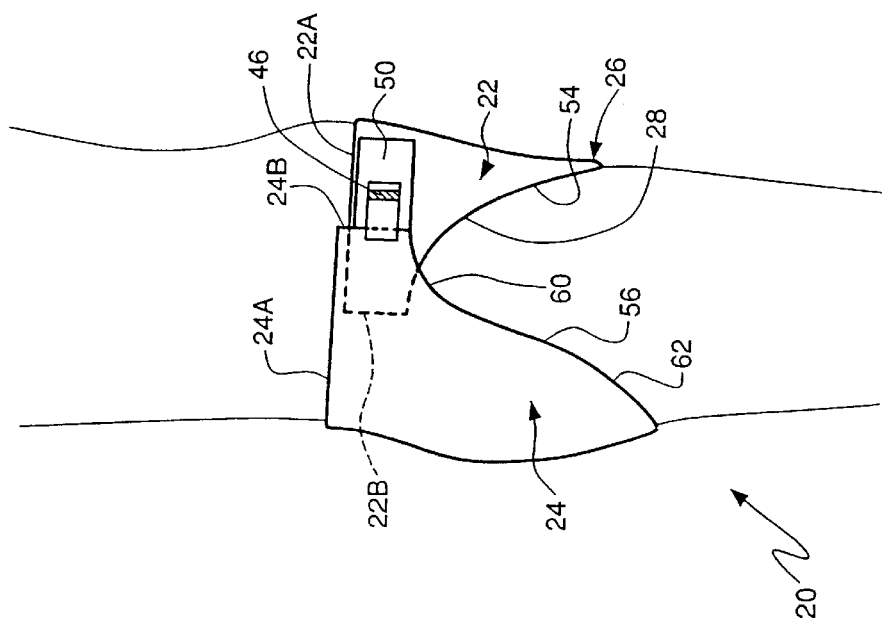
FIG. 2 is a side elevational view, like that of FIG. 1, but showing the person wearing a protective undergarment, e.g., brief, constructed in accordance with this invention.
Figure 1:
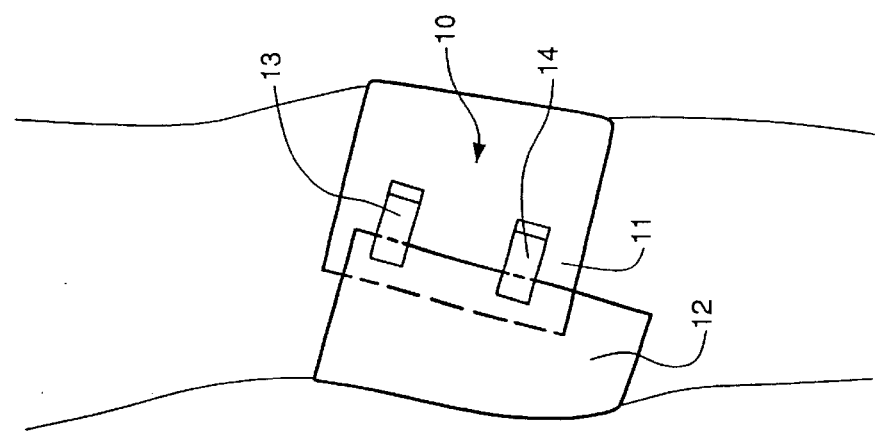
FIG. 1 is a side elevational view of a person wearing a prior art disposable protective undergarment, e.g., a Supreme adult brief.

Referring now to the various figures of the drawing wherein like reference characters refer to like parts, there is shown in FIG. 2 a disposable protective garment 20 constructed in accordance with one embodiment of this invention. The undergarment of FIG. 2 is in the form of a brief and is particularly constructed to enable it to be readily put on or taken off, like conventional disposable baby diapers.

Figure 3:
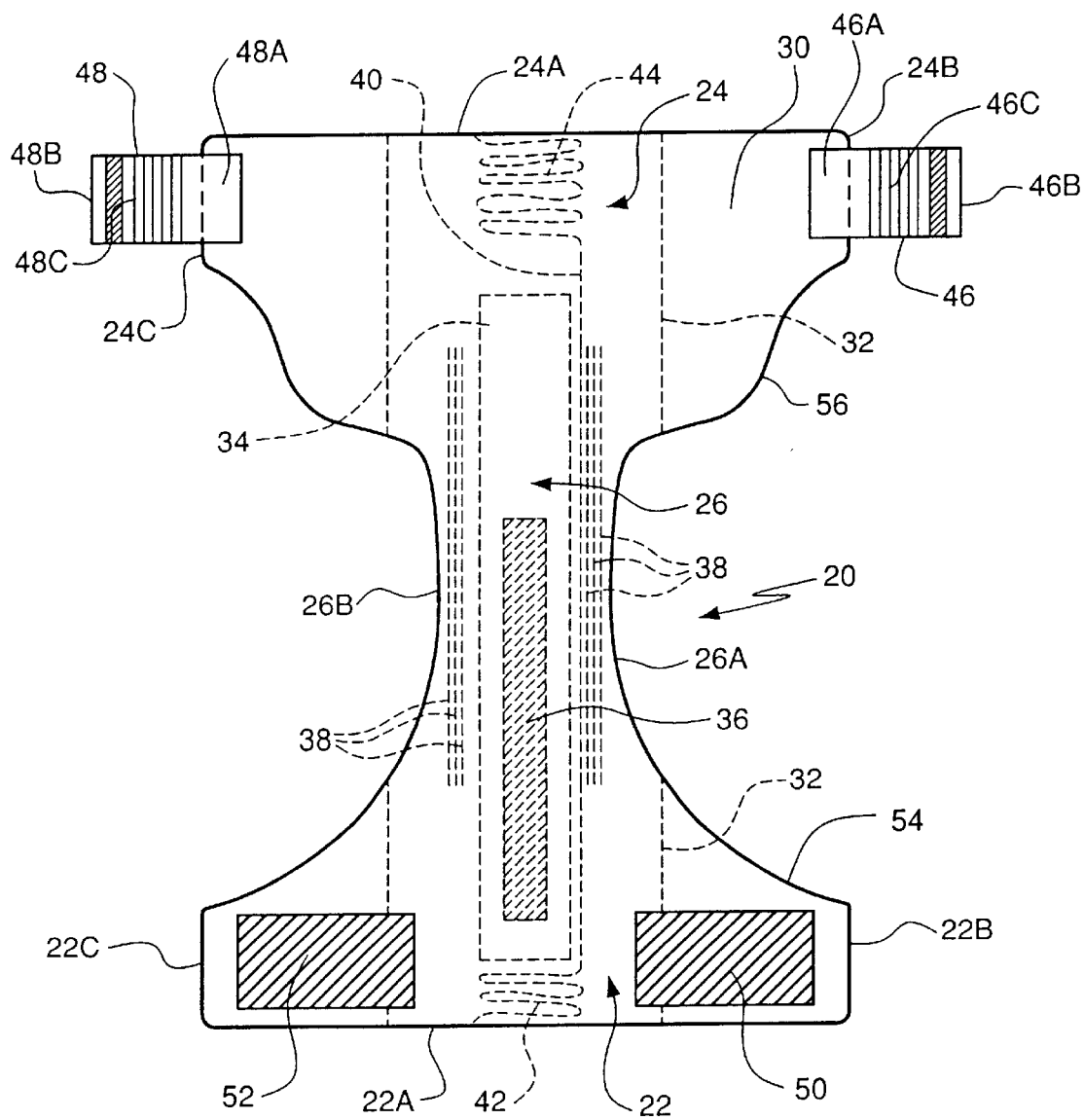
FIG. 3 is a top plan view of the undergarment shown in FIG. 2.

As best seen in FIGS. 2 and 3, the brief 20 basically comprises a chassis made up of a front section 22, a back section 24, and a central section 26. The front section 22 includes a top front edge 22A and pair of front side edges, 22B and 22C. In the embodiment shown each front side edge 22B and 22C is linear, but such edges can be of other shapes, if desired. In a similar manner, the back section 24 includes a top back edge 24A and pair of back side edges, 24B and 24C. In the embodiment shown each back side edge 24B and 24C is linear, but such edges can be of other shapes, if desired. The central or intermediate section 26 includes a pair of central side edges 26A and 26B disposed on opposite sides of the central section 26. The central side edges 26A and 26B will be described in detail later. Suffice it for now to state that each of the central side edges is an ergonomically shaped recess to form a respective leg opening 28 (FIG. 2) in the brief 20, when it is mounted in place on the wearer, with each leg opening closely conforming to the contiguous portion of the wearer's body in the interest of comfort and to minimize leakage of waste fluid from the brief. To further that end, as will also be discussed later, the central side edges 26A and 26B forming the leg openings 28 are elasticized. The portions of the chassis contiguous with the front side edges 22B and 22C form what are commonly referred to as the front section "ears" of the chassis, while the portions of the chassis contiguous with the back side edges 24B and 24C form the back section ears of the chassis. As is conventional, the respective front section ears of the chassis are arranged to be overlapped somewhat by the respective back section ears of the chassis and to be releasably secured together to form the respective leg openings of the chassis and to mount the brief in place as shown in FIG. 2.

Referring now to FIG. 3, the details of the chassis will now be described. To that end the chassis is composed of a single outer sheet 30 of a cloth-like, non-woven, breathable material having a generally rectangular shape with a pair of asymmetrical recesses cut in the sides thereof to form the heretofore identified central side edges 26A and 26B. The outer sheet 30 is preferably hydrophobic 15.0 gsm SMS (spunbond/meltblown/spunbond) non-woven material, available from Avgol Nonwoven Industries of Holon, Israel. For a medium size brief (like shown in FIG. 4) the length of the sheet 30, i.e., the distance between the front top edge 22A and the back top edge 24A is approximately 825 mm, the width of the sheet between the side edges 22B/22C and 24B/24C is approximately 635 mm, and the width of the sheet between the central side edges 26A/26B at their closest point of approach is 230 mm. Other conventional materials can be used in lieu of the exemplary SMS material.

In order to render brief 20 moisture impervious, a plastic film or moisture barrier sheet 32 is disposed centered across a major portion of the inner surface of the sheet 30 and extending from the top front edge 22A to the top back edge 24A. The barrier sheet 32 is approximately 230 mm wide and preferably a 0.6 mil polyethylene film available from Pliant Corporation of Newport News, Va., under the trade designation XP-1842D. Other conventional materials can be used in lieu of the exemplary film material to form the moisture barrier sheet.

In the exemplary embodiment shown herein, the barrier sheet 32 is adhesively secured to a cover-stock material (not shown—but to be described later) located on the underside of an absorbent core 34. The barrier sheet 32 may be rectangular in shape and of a width sufficient so that it extends up to the closest point that the central edges 26A and 26B reach each other, or as shown in FIG. 3 may be of a width to extend slightly beyond those points and into the ears of the chassis adjacent the front side edges 22B/22C and into the ears of the chassis adjacent the back side edges 24B/24C.

The absorbent core 34 is of a generally rectangular shape and extends for a substantial length of the chassis, i.e., from a point closely adjacent the top front edge 22A to a point somewhat adjacent the top back edge 24A. In particular, the core is not centered longitudinally. Rather, as best seen in FIG. 3, the distance from the end of the core to the adjacent top front edge 22A is less than the distance from the other end of the core to the adjacent top back edge 24A so that the core is located to encompass the insult zone, i.e., the zone at which the urine or feces, makes initial contact with the brief, and extending beyond the core on all sides. In accordance with an exemplary embodiment of this invention the core 34 preferably comprises a blanket of cellulosic fibers, e.g., wood pulp fluff made of up bleached sulfate wood pulp containing soft wood fibers, such as that available from International Paper of Tuxedo, N.Y., under the trade designation Super Soft Plus. The core preferably contains hydrogel polymer particulates (known as Super Absorbent Polymer or "SAP") such as ASAP-2260 available from BASF Corporation of Portsmouth, Va., co-mingled with the cellulosic fibers. If desired, these materials may be optionally enwrapped in tissue. For a medium size brief (like shown in FIG. 4) the length of the core is approximately 680 mm, the pulp of the core is 41 gms and the SAP is 11.5 gms. The amount of each absorbent material and SAP/fluff ratio depends on the size of the protective underwear and whether or not a transfer or fluid acquisition layer component (to be described hereinafter) is to be included in the chassis. The superabsorbent particles (SAP) are preferably included in the core to enhance its absorbency. Other conventional materials can be used to make up the core, with or without any absorbency enhancing materials.

The center of core 34 is overlaid with an internal layer of hydrophillic 15.0 gsm SBPP (spunbond polypropylene) non-woven coverstock (not shown), available from Avgol Non-woven Industries of Holon, Israel, under the trade designation ZEBRA° Zone Coated. An external cover-stock (not shown), e.g., hydrophobic 15.0 gsm SBPP (spunbond polypropylene) nonwoven material available from BBA Nonwovens of Simpsonville, S.C. extends beyond the perimeter of the core is adhesively secured to the moisture barrier sheet 32.

A fluid acquisition layer or sheet 36 is disposed on top of the core and beneath the internal coverstock layer, in the vicinity of the insult zone. As is known a fluid acquisition layer is utilized to facilitate and manage the transfer of the fluid waste material into the core. To that end, in the exemplary embodiment shown herein, the fluid acquisition layer 36 is a rectangular member which is smaller in width and length than the core, e.g., for a medium size brief the core is 680 mm long and 150 mm wide. The fluid acquisition layer 36 can be a single layer or multiple layers of any suitable material. For example, the fluid acquisition layer can be thru-air bonded/carded web, a spunbond bicomponent non-woven web, a web of cross-linked cellulosic fibers, apertured 3D film or the like, which may be surface embossed. One particularly suitable material is TABICO (Through-Air Bonded Carded Web) available from PGI Nonwovens of Morresville, N.C., under the trade designation #4169 and has an overall basis weight of 40 gsm. Other fluid acquisition layers used in disposable absorbent articles can be used in lieu of the exemplary layer.

In order to enable the central side edges 26B and 26C to closely conform to the legs of the wearer when the brief 20 is in place, each of the central side edges 26A and 26B is elasticized. To that end plural, e.g., three, pre-stretched white elastic threads or filaments 38 are adhesively secured to the moisture barrier sheet 32 along portions thereof extending alongside the respective sides of the core 34. The barrier sheet 32 having the threads 38 secured thereto is adhesively secured to the coverstock (not shown) on the underside of the core 34. In the exemplary embodiment shown herein each of the three threads 38 on each side of the core preferably comprises LYCRAO® XA spandex available from E. I. DuPont DeNemours & Company of Wilmington, Del., under the trade designation 540 decitex. Other elasticizing means used in disposable absorbent articles can be used in lieu of the exemplary threads.

In order to enable the chassis to closely conform to the waist of the wearer when the brief 20 is in place, the portion of the chassis contiguous with the front top edge 22A and the portion of the chassis contiguous with the back top edge 24A is elasticized. To that end an elastic thread or ribbon 40 is adhesively secured to the inner surface of the sheet 30. The filament or ribbon undulates back and forth to form plural transversely extending legs 42 adjacent the front top edge 22A of the chassis and plural transversely extending legs 44 adjacent the back top edge 24A of the chassis. The undulating legs 42 and 44 of the thread or ribbon 40 are pre-stretched and are adhesively secured in place. In the exemplary embodiment shown herein the thread or ribbon 40 preferably comprises LYCRA® XA spandex available from E. I. DuPont DeNemours & Company of Wilmington, Del., under the trade designation 740 decitex. Other elasticizing means used in disposable absorbent articles can be used in lieu of the exemplary threads or ribbon. The adhesive used to adhere the thread or ribbon 40 is preferably an elastic specific adhesive, such as hot melt #34-543A available from National Starch & Chemical Company of Bridgewater, N.J.

A cloth-like non-woven sheet (not shown) of the same size and shape as the sheet 30 is disposed over the acquisition layer 36 and underlying core 34 and is adhesively secured in place to the inner surface of the sheet 30. This sheet forms the body contacting surface of the brief when it is worn. Any suitable construction adhesive or hydrophillic adhesive, such as Construction Hot Melt adhesive available from National Starch & Chemical Company of Bridgewater, N.J., under the trade designation #34-563A, can be used to secure the body engaging sheet to the chassis. In fact, the adhesive or any other suitable adhesive may be utilized to secure other components of the chassis to each other.

When the chassis is assembled the fluid acquisition layer 36, the underlying core and the adhesive filaments 38 and 40 are interposed and adhesively secured between the inner surface of the barrier sheet 32 and the body engaging sheet.

In order to secure the ear portions of the brief 20 to each other to mount the brief on the wearer, the subject invention makes use of only two fastening members 46 and 48, e.g., fastening tapes, one on each face of the chassis at the back section 24. These tapes are arranged to be releasably secured to respective landing zones 50 and 52 located on the front surface of the front section 22 of the chassis. By using only two fastening members, the subject invention can be put on or taken off more readily and quickly than the prior art adult briefs (which make use of two fastening tapes on each side of the undergarment). The ability to use only one fastening member, e.g., tape, on each side of the brief 20 is the result of the ergonomic shape of the central section side edges 26A and 26B, as will be described later.

However, before describing those side edges, a short description of the fastening members 46 and 48 is in order. To that end each tape is a generally rectangular shaped strip of material having one end which is fixedly adhesively secured to the outer surface of the sheet 30 so that a free end of the tape extends beyond the side edge of the sheet to which it is secured. For example, one end 46A of the tape 46 is fixedly secured, e.g., glued, to the outer surface of the sheet 30 closely adjacent the back side edge 24B, and is oriented transversely to the longitudinal axis of the chassis so that the free end 46B of the tape 46 extends beyond the side edge 24B. In a similar manner one end 48A of the tape 48 is fixedly secured, e.g., glued, to the outer surface of the sheet 30 closely adjacent the other back side edge 24C, and is oriented transversely to the longitudinal axis of the chassis and aligned with the tape 46 so the free end 48B of the tape 48 extends beyond the back side edge 24C. The inner surface of the free end 46B of the tape 46 includes a large plurality of very small hook-like members (not shown) for releasable securement to the landing zone 50. In a similar manner the inner surface of the free end 48B of the tape 48 includes a large plurality of very small hook-like members (not shown) for releasable securement to the landing zone 52.

Each landing zone 50 and 52 is in the form of a rectangular patch secured to the outer surface of the sheet 30 at the front section 22 slightly below the front top edge 22A and adjacent the front section's ears. Each landing zone patch comprises a large plurality of very small loops (not shown) projecting therefrom for releasable engagement by the large plurality of hooks of the tapes 46 and 48. In accordance with a preferred embodiment of this invention for a medium size brief, each landing zone is approximately 102 mm wide by approximately 76 mm high.

The fastening tapes 46 and 48 includes an extendable or stretchable central portion 46C and 48C, respectively, located between the fixedly secured end of the tape and the free end of the tape to enable each tape to be stretched longitudinally to facilitate its releasable securement to the landing zones 50 and 52 on the front section 22 of the chassis.

In accordance with a preferred embodiment of this invention each of the fastening tapes 46 and 48 is available from Koester GmbH & Co. KG of Altendorf, Germany, under the trade designation CP-2/EM 67-5. Other releasably securable fastening tapes can be utilized in lieu of the foregoing hook and loop fastening system. For example, the tapes 46 and 48 may include releasably securable adhesive areas on the inner surface of their free ends in lieu of the plurality of hooks. In such an alternative embodiment the landing zones can be constructed, e.g., comprise a plastic film, to releasably receive the adhesive areas of the tapes. If the fastening tapes are of the adhesive type, a releasable liner or cover is preferably located on the adhesive of the tape to protect it from degradation or soiling until it is ready to be used.

Figure 4:
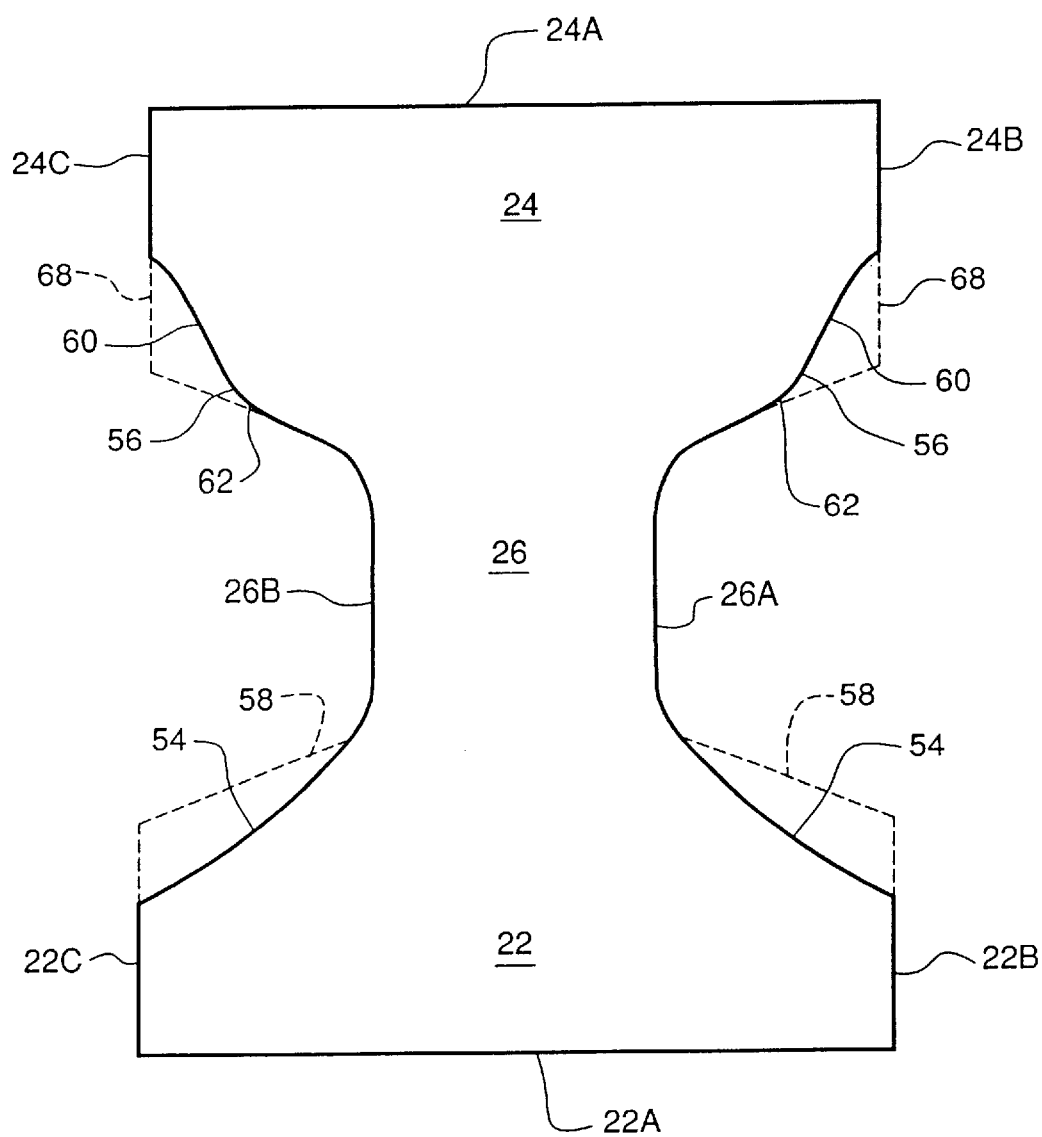
FIG. 4 is a top plan view of the undergarment shown in FIG. 2 of a small or medium size, and with the profile of a prior art small or medium size undergarment shown by the phantom lines in this figure.
Figure 5:
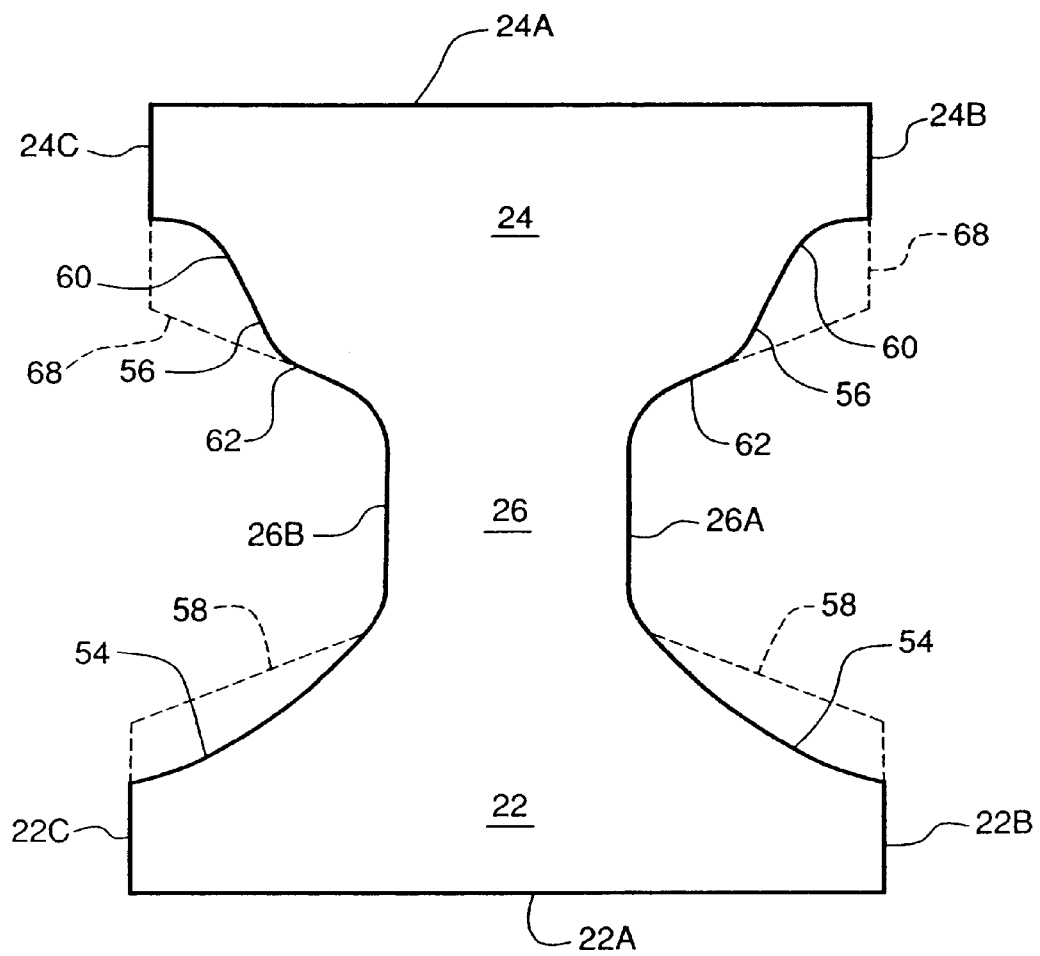
FIG. 5 is a top plan view of the undergarment shown in FIG. 2 of a large size, and with the profile of a prior art large size undergarment shown by the phantom lines in this figure.

Referring to FIGS. 3–5 the ergonomic shape of the central side edges 26A and 26B to provide the various advantages of this invention will now be described. To that end, as can be seen these two central side edges are mirror images of each other. In the interest of brevity only the shape of the central side edge 26A will be described in detail herein. The central side edge 26A basically comprises first central edge region 54 and a second central edge region 56. The first central edge region 54 of the central side edge 26A is of a concave arcuate shape and is located contiguous with the front side edge 22B. The concave arcuate shaped edge region 54 produces a "high-cut" leg opening 28 when the brief is in place, by shortening the length of the front side edge 22B of the aforementioned prior art Supreme brief. The corresponding portion of the leg opening for the prior art Supreme brief is shown by the phantom lines designated by the reference number 58 in FIGS. 4 and 5 to graphically demonstrate the high-leg cut inventive feature of the subject brief. FIG. 2 shows the brief 20 in place, with the high leg-cut opening produced thereby.

The second central edge region 56 is of a generally S-shape having an arcuate concave portion 60 (FIGS. 4 and 5) and a contiguous arcuate convex portion 62. The arcuate concave portion 60 is located contiguous with the back side edge 24B and shortens the length of that back side edge from that of the aforementioned prior art Supreme brief. In this regard, as can be seen in FIGS. 4 and 5 the corresponding portion of the leg opening for the heretofore identified prior art Supreme brief is shown by the phantom lines designated by the reference number 68. As best seen in FIG. 2, the arcuate concave portion 60 cooperates with the arcuate concave shaped edge region 54 contiguous with the brief's front side edge 22B to produce the high-cut leg opening 28 when the brief is in place.

The arcuate convex portion 62 of the central edge region 56 is contiguous with the concave portion 60. Being convex, the arcuate portion 62 provides additional coverage of the brief's chassis over the portions of the wearer's buttocks contiguous with the wearer's leg as best seen in FIG. 2, than would otherwise result if the central edge region 56 were shaped like the central edge region 54. Thus, the brief 20 can be said to provide "full buttocks" coverage.

As mentioned earlier FIGS. 4 and 5 represent the outer profile of the chassis of an undergarment or brief constructed in accordance with this invention for small and medium sizes (FIG. 4) and large sizes (FIG. 5). To that end, as can be seen in FIG. 5 the concave portion 60 of the S-shaped central edge region 56 can be made so that it exhibits a greater degree of concavity when the subject invention is used for large sized briefs than the concave portion 60 shown in FIG. 4. The small/medium brief is arranged to provide moderate to heavy incontinent protection, while the large brief is arranged to provide heavy protection.

As should be appreciated from the foregoing, the leg cut-out pattern forming the central side edges 26A and 26B produces a high-cut opening at the front leg area, thereby reducing tension and stress when the person wearing the brief is in a sitting position or when the wearer is walking. This reduction in stress should result in improving comfort. Moreover, the "full buttocks coverage" at the buttocks-back leg area should reduce leakage. Another advantage of the subject invention relates to its use of the shorter length of the side edges 22B/22C of the front section 22 and the side edges 24B/24C of the back section 24, since they enable the brief 20 to require only a single attachment means, e.g., fastening tape, at each side of the brief, making the brief more convenient to use when putting it on or removing and also decreasing manufacturing costs. Other advantageous features of the brief are the inclusion of the mechanical refastening means, e.g., the cooperating hook and loop fasteners of the tapes, for improved convenience. Moreover, the fact that the fasteners are stretchable, alone or in combination with the elastic waist of the brief provides for improved fit and body conformance. The cloth-like and breathable outer cover further enhances wearing comfort. If desired, conventional standing leg cuffs (not shown) may also be added to the brief, to further improve non-leakage and absorbency performance. Further still, some odor control medium, e.g., sodium bicarbonate, may be incorporated into the brief.

It should be pointed out at this juncture that the materials as described heretofore to make up the invention are merely exemplary of numerous materials that can be used for the various components. Thus, other conventional materials can be used for the chassis, its components, and the fastening members.

Without further elaboration, the foregoing will so fully illustrate our invention that others may, by applying current or future knowledge, adopt the same for use under various conditions of service.

We claim:

1. A protective underwear arranged to be worn by an adult person to trap and collect loose or liquid waste products of the person, said underwear having a front section, a back section and a central section, said front section having a front top edge and a pair of front side edges, said back section having a back top edge and a pair of back side edges, said front side edge and said back side edge being approximately equal in length, the width of said front section between said pair of front side edges being the approximately the same as the width of said back section between said pair of back side edges, said central section having a pair of central side edges and being located between said front and back sections, said back section including a pair of fastening members secured thereto, with one of said fastening members extending along one of said back side edges for most of the length of said one of said back side edges and also extending beyond said one of said back side edges and the other of said fastening members extending along the other of said back side edges for most of the length of said other of said back side edges and also extending beyond said other of said back side edges, each of central side edges having a first central edge region and a second central edge region, said first central edge region being of a concave arcuate shape, said second central edge region being of a generally S-shape having a concave portion and a convex portion, said first central edge regions being contiguous with respective ones of said front side edges, said convex portions of said second central edge regions being contiguous with respective ones of said first central edge regions and said concave portions of said second central edge regions being contiguous with respective ones of said rear side edges, said fastening members being arranged to be secured to respective portions of said front section to mount said underwear in place on the wearer, with said central section being located adjacent the wearer's crotch, whereupon each of said first central regions of said central side edges provide a high cut area contiguous with the front of the wearer's leg adjacent the wearer's crotch, said high cut area being located close to said top edges of said front and back sections and whereupon each of said convex portions of said second central edge regions provides substantial coverage of the wearer's buttocks.

2. The protective underwear of claim 1 wherein said underwear comprises only two of said fastening members.

3. The protective underwear of claim 1 wherein said fastening members are releasably securable to said front section.

4. The protective underwear of claim 3 wherein said fastening members include one component of a hook and loop fastening system, and wherein said front section includes the other component of said hook and loop fastening system.

5. The protective underwear of claim 1 wherein said fastening members are stretchable.

6. The protective underwear of claim 5 wherein said fastening members are releasably securable to said front section.

7. The protective underwear of claim 6 wherein said fastening members include one component of a hook and loop fastening system, and wherein said front section includes the other component of said hook and loop fastening system.

8. The protective underwear of claim 1 wherein said underwear comprises an outer sheet, at least a portion of which is rendered moisture impermeable, an inner sheet at least a portion of which is moisture permeable, and an absorbable core located between said inner and outer sheets.

9. The protective underwear of claim 8 wherein said core is formed of a highly moisture absorbent material.

10. The protective underwear of claim 9 wherein said core is formed of pulp and a superabsorbent particulate.

11. The protective underwear of claim 8 additionally comprising a fluid acquisition layer located between said inner sheet and said core.

12. The protective underwear of claim 1 wherein said central side edges include portions which are elasticized.

13. The protective underwear of claim 12 additionally comprising at least one elastic thread for elasticizing said portions of said central side edges.

14. The protective underwear of claim 1 wherein a portion of said front section adjacent said front top edge is elasticized.

15. The protective underwear of claim 14 additionally comprising at least one elastic thread for elasticizing said portion of said front section.

16. The protective underwear of claim 1 wherein a portion of said back section adjacent said back top edge is elasticized.

17. The protective underwear of claim 16 additionally comprising at least one elastic thread for elasticizing said portion of said back section.

18. The protective underwear of claim 16 wherein a portion of said front section adjacent said front top edge is elasticized.

19. The protective underwear of claim 18 additionally comprising at least one elastic thread for elasticizing said portion of said front section.

20. The protective underwear of claim 1 wherein said inner sheet comprises a non-woven material.

21. The protective underwear of claim 20 wherein said non-woven material is a spunbond/meltblown/spunbond.

22. The protective underwear of claim 1 additionally comprising a plastic film to render at least a portion of said outer sheet moisture impermeable.

23. The protective underwear of claim 22 wherein said plastic film is confined to the portion of the underwear comprising the central section and the contiguous portions of the front and back sections.

24. The protective underwear of claim 23 wherein said inner sheet comprises a non-woven material.

* * * * *